_United States Patent_ [19]

Ide et al.

[11] Patent Number: 4,791,196

[45] Date of Patent: Dec. 13, 1988

[54] CRYSTALLINE CEPHEM CARBOXYLIC ACID ADDITION SALT

[75] Inventors: Junya Ide; Koichi Fujimoto, both of Tokyo, Japan

[73] Assignee: Sankyo Company Limited, Tokyo, Japan

[21] Appl. No.: 100,204

[22] Filed: Sep. 23, 1987

[30] Foreign Application Priority Data

Sep. 26, 1986 [JP] Japan ................................. 61-227460

[51] Int. Cl.$^4$ .................. C07D 501/46; A61K 31/545
[52] U.S. Cl. ..................................... 540/227; 540/222
[58] Field of Search ................ 544/227, 222; 514/195, 514/206

[56] References Cited

U.S. PATENT DOCUMENTS 4,665,066  5/1987  Morin ................................. 540/227

FOREIGN PATENT DOCUMENTS 60-67483  4/1985  Japan .

Primary Examiner—Nicholas S. Rizzo
Attorney, Agent, or Firm—Frishauf, Holtz, Goodman & Woodward

[57] ABSTRACT

A storage stable form of the crystalline sulfate of 7-[2-(2-aminothiazol-4-yl)-(Z)-2-methoxyiminoacetamido]-3-[5-(2-hydroxyethyl)-4-methylthiazoliomethyl]-3-cephem-4-carboxylate has a specified X-ray diffraction pattern and is prepared by adding aqueous sulfuric acid to an aqueous solution of the compound under controlled conditions.

16 Claims, No Drawings

CRYSTALLINE CEPHEM CARBOXYLIC ACID ADDITION SALT

BACKGROUND TO THE INVENTION

The present invention relates to a novel composition of matter comprising a specific crystalline form of the sulfate of the cephalosporin derivative known as 7-[2-(2-aminothiazol-4-yl)-(Z)-2-methoxyiminoacetamido]-3-[5-(2-hydroxyethyl)-4-methylthiazoliomethyl]-3-cephem-4-carboxylate.

This cephalosporin derivative is known and is described, for example, in Japanese Patent Application Kokai (i.e. as laid open to public inspection) No. 67483/85 and in European Patent Publication No. 186 463. It has the formula:

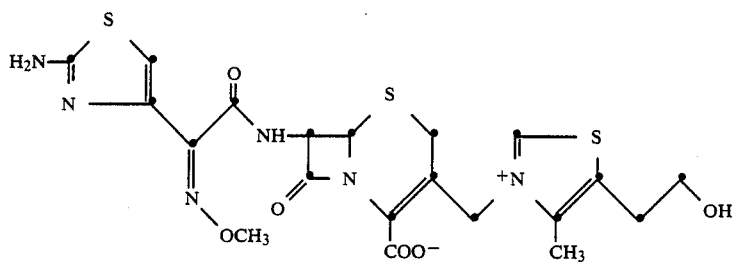

(I)

The above-mentioned Japanese Patent Application refers to the hydrochloride. hydrobromide, nitrate, phosphate, methanesulfonate and p-toluenesulfonate of the compounds described therein including the compound of formula (I). The aforementioned European Publication refers to the hydrochloride, hydrobromide, phosphate and sulfate of the compounds described therein including the compound of formula (I). The prior art specifications do not refer to the form in which the salts may be obtained, but conventional methods of preparing salts (including the methods referred to in those prior art specifications) would inevitably lead to the amorphous form of the salts. However, the compound of formula (I) and all of its salts so far investigated have been found by us to be so unstable at room temperature that they cannot, in practice, be used, and it has been necessary to find some way of improving the stability of the compound in order for it to be used practically as a drug. Hence, the only forms of this cephalosporin derivative and its salts heretofore known are too unstable to find any practical use.

We have now surprisingly found that a certain specific crystalline form of the sulfate of this compound shows a remarkable and altogether unexpected stability, which makes this cephalosporin derivative, for the first time, a practical proposition for clinical use.

BACKGROUND TO THE INVENTION

It is, therefore, an object of the present invention to provide the aforementioned cephalosporin derivative in a form sufficiently stable for practical therapeutic use.

It is a further and more specific object of the invention to provide a crystalline form of the sulfate of this compound in a form sufficiently stable for practical therapeutic use.

It is a still further object of the present invention to provide a process for preparing this crystalline form of the sulfate.

Thus, the present invention provides a crystalline form of 7-[2-(2-aminothiazol-4-yl)-(Z)-2-methoxyiminoacetamido]-3-[5-(2-hydroxyethyl)-4-methylthiazoliomethyl]-3-cephem-4-carboxylate sulfate, which is shown by formula (II):

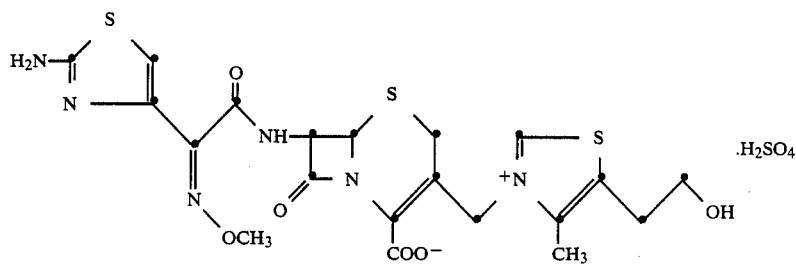

(II)

(abbreviated hereinafter to "S-form crystals") which is characterised by the following X-ray diffraction data determined by the powder method using the copper $K_\alpha$-ray, $\lambda=0.154$ nm, with an error in measurement of relative intensity within $\pm 5\%$ (in this Table, d indicates crystal lattice and $I/I_{max}$ indicates relative intensity):

| Phase d | Relative intensity $I/I_{max}$ | Phase d | Relative intensity $I/I_{max}$ |
|---|---|---|---|
| 111.11 | 100 | 3.81 | 61 |
| 7.02 | 60 | 3.74 | 86 |
| 6.10 | 29 | 3.69 | 39 |
| 5.75 | 24 | 3.61 | 79 |
| 5.03 | 24 | 3.53 | 59 |
| 4.69 | 92 | 3.40 | 38 |
| 4.51 | 27 | 3.35 | 32 |
| 4.47 | 38 | 3.25 | 30 |
| 4.38 | 42 | 3.15 | 83 |
| 4.31 | 76 | 2.74 | 25 |
| 4.00 | 32 | 2.67 | 35 |
| 3.96 | 27 | | |

DETAILED DESCRIPTION OF THE INVENTION

The S-form crystals of this invention may be prepared by adding dilute aqueous sulfuric acid to an aqueous solution of the compound of formula (I) in an amount sufficient to provide at least an equimolar amount of sulfuric acid with respect to the compound of formula (I), whilst cooling, preferably with ice. The aqueous acid preferably has a concentration of from 3% to 20% w/v, more preferably from 5% to 10% w/v and the amount of acid is preferably from 1 to 1.5 moles per mole of said compound of formula (I), more preferably from 1.1 to 1.2 moles.

More specifically, the S-form crystals may be prepared from the free compound represented by the formula (I) by dissolving the compound in water, and, whilst stirring the resulting solution on an ice bath, adding dilute (from 3% to 20% w/v) sulfuric acid in an amount sufficient to provide from 1 to 1.5 mole of sulfuric acid, more preferably from 5% to 10% w/v sulfuric acid and more preferably from 1.1 to 1.2 mole of sulfuric acid. After they have been cooled with ice water, the separated crystals may be collected by filtration, washed (e.g. with aqueous ethanol or ethanol) and washed again (e.g. with diethyl ether or a small quantity of water). The crystals obtained may be dried at 20° C. to 25° C. to afford the S-form crystals.

The S-form crystals can alternatively be prepared by suspending or dissolving an amorphous salt, e.g. the amorphous sulfate, hydrochloride or nitrate in water neutralizing it with an alkali, e.g. an alkali metal or alkaline earth metal carbonate or bicarbonate such as sodium bicarbonate, and then treating the resulting solution with dilute sulfuric acid as mentioned above and in a similar way to that mentioned above.

Since the S-form crystals obtained by these procedures are isolated from aqueous media, they will normally contain at least some water. generally in an amount from 0 to 5% by weight of the compound of formula (II), depending on the drying conditions. It is believed that at least some of this water is hygroscopic as the water content may decrease with time, but it is not clear if any is bound to the compound. However, in most cases, the S-form crystals of the present invention are believed not to contain water of crystallisation.

If desired, the S-form crystals of the present invention may be mixed with one or more pharmaceutically acceptable diluents, carriers, adjuvants and/or buffer substances to form a pharmaceutical composition. This may then, if require, be dissolved in a suitable injectible liquid at the point of use for injection. Examples of suitable injectible liquids which may be employed include polyglycols and/or water, both essentially sterile. Examples of the buffer substances which may be employed include phosphate buffer solutions, sodium bicarbonate and/or sodium carbonate.

The dose of the S-form crystals of the invention will, of course, vary with the nature of the disease to be treated, the symptoms, age, condition and body weight of the patient and the route and time of administration; however, for an adult human patient, a daily dose of from 0.2 to 3.0 grams is preferred and this may be administered in a single dose or in divided doses.

The S-form crystals of the present invention have excellent antibacterial activity against cephalosporinase-producing bacteria, whether they be gram-positive or gram-negative, of an order comparable with the free compound of formula (I) itself. They also have very low toxicity and are thus of potentially great value as chemotherapeutic agents.

Moreover, the S-form crystals do not decompose after standing for several months at a range of temperatures varying from room temperature to 60° C., thus showing that this crystalline form has much higher stability than does the amorphous form.

The invention is further illustrated by the following Examples.

EXAMPLE 1

23.2 g of 7-[2-(2-aminothiazol-4-yl)-(Z)-2-methoxyiminoacetamido]-3-[5-(2-hydroxyethyl)-4-methylthiazoliomethyl]-3-cephem-4-carboxylate were dissolved in 50 ml of water. Dilute sulfuric acid [which had been prepared from 4.64 g of concentrated (95% w/v) sulfuric acid and 60 ml of water] were then added to this solution on an ice bath, whilst stirring. The mixture was allowed to stand for 3 hours. after which the separated crystals were collected by filtration, washed with 50% v/v aqueous ethanol, absolute ethanol and diethyl ether, in that order, and dried for 48 hours in vacuo at room temperature to afford 16.8 g of the desired S-form crystals.

The S-form crystals obtained by the above procedure showed the elemental analysis and NMR spectrum shown below. The X-ray diffraction data are as given above.

Elemental analysis of the crystals gave the following results:

C, 37.18%; H, 3.71%; N, 13.03%; S, 19.81%.
and a water content of 1.7% w/w (Karl Fischer's titration)

Nuclear Magnetic Resonance Spectrum: (270 MHz, hexadeuterated dimethyl sulfoxide) δ ppm: 2.39 (3H, singlet); 3.02 (2H, triplet, J=5 Hz); 3.38 (2H, singlet); 3.65 (3H, triplet, J=5 Hz); 3.83 (3H, singlet); 5.18 (1H, doublet, J=5 Hz); 5.39–5.54 (2H, multiplet); 5.85 (1H, doublet of doublets, J=5 Hz, J=8 Hz); 6.73 (1H, singlet); 7.22 (2H, singlet).

EXAMPLE 2

(a) 271 mg of 7-[2-(2-aminothiazol-4-yl)-(Z)-2-methoxyiminoacetamido]-3-[5-(2-hydroxyethyl)-4-methylthiazoliomethyl]- 3-cephem-4-carboxylate were dissolved in 0.5 ml of water. 0.1 ml of concentrated hydrochloric acid, followed by 5 ml of ethanol, were then added to the solution, to give a small amount of insoluble matter. This insoluble matter was filtered off, and the filtrate was mixed with 10 ml of ethanol. The mixture was then allowed to stand for 2 hours in a refrigerator at −5° C. The resulting crystals were collected by centrifugation, washed with ethanol and then with acetonitrile and dried to afford 253 mg of the amorphous hydrochloride of compound (I).

(b) 10.6 g of the amorphous hydrochloride of compound (I) obtained as described in step (a) above were dissolved in 60 ml of water, and then 1.66 g of sodium bicarbonate were added, whilst stirring at room temperature, to the resulting solution. Dilute sulfuric acid (which had been prepared from 2.2 g of 95% w/v sulfuric acid and 15 ml of water) was then added to the solution. The mixture was allowed to stand for 30 minutes at room temperature and then for 1 hour in an ice bath. The separated crystals were collected by filtration. washed with a small amount of water and dried in vacuo for 48 hours at room temperature to afford 6.35 g of S-form crystals.

EXAMPLE 3

(a) 266 mg of 7-[2-(2-aminothiazol-4-yl)-(Z)-2-methoxyiminoacetamido]-3-[5-(2-hydroxyethyl)-4-methylthiazoliomethyl]-3-cephem-4-carboxylate were dissolved in 1 ml of water, and the resulting solution was cooled in an ice bath. 0.984 ml of 1N aqueous nitric acid were then added to the solution, and the resulting mixture was allowed to stand for 3 hours in a refrigerator. The matter which separated was collected by filtration, washed with a small amount of cool water and then with ethanol, and dried to afford 154 mg of the amorphous nitrate of compound (I).

(b) S-form crystals were obtained by the same procedure as in Example 2-(b) from the amorphous nitrate of compound (I) obtained as described in step (a) above.

COMPARATIVE EXAMPLES

A Procedure similar to that described in Example 1 was repeated, except that the dilute sulfuric acid used to prepare the S-form crystals was replaced by, in each case, one of the following acids: hydrobromic acid, nitric acid, phosphoric acid, phosphorous acid, maleic acid, oxalic acid, methanesulfonic acid and p-toluenesulfonic acid. In the case of the nitrate, by carrying out the crystallization very carefully, it was possible to prepare crystals; in every other case, however, the product was an amorphous salt of limited stability.

The products of Examples 1-3 and the Comparative Examples were tested for stability and the results are shown in the following Experiments:

EXPERIMENT 1

The sulfate of the amorphous compound and the S-form crystals prepared as illustrated in Exaples 1-3 were compared for stability by the following test.

The samples were weighed in vials which were then sealed with gum stoppers. The vials were then allowed to stand at either 40° C. or 50° C. for 2, 4 or 7 weeks. At the end of the respective test period, the contents of compound (I) in the vials were determined by liquid chromatography. The results are shown below.

| Temperature °C. | 50 | | | | 40 | |
|---|---|---|---|---|---|---|
| Standing period, Week | 0 | 2 | 4 | 7 | 4 | 7 |
| Amorphous | 100% | 90% | 86% | 80% | 89% | 85% |
| S-form crystal | 100% | 99% | 99% | 100% | 100% | 100% |

The amorphous samples were not good for practical use because of decomposition of the compound (I) by 15% after standing at 50° C. for 4 weeks or at 40° C. for 7 weeks. On the other hand, the S-form crystal samples of this invention are very stable as can be seen from the above Table.

EXPERIMENT 2

In this experiment the nitrate was employed in crystalline form, the sulfate was in both crystalline and non-crystalline forms and the other salts were all in an amorphous, powdery form prepared by dissolving the free carboxylic acid in water, adding an acid to the solution and then precipitating the product with ethanol. The methanesulfonate was so strongly hygroscopic that it was practically impossible to weigh it out, and so no quantitative analysis was made from the outset; in any case, this property clearly made the compound unsuitable for therapeutic use. The maleate was sparingly soluble in water but was initially soluble in a phosphate buffer solution at pH 7.4; however, it became insoluble within 1 week of starting the stability test, and so no quantitative analysis was carried out at weeks 1 and 2. Similar phenomena were observed with the phosphate. Phosphite and oxalate, and so, again, no quantitative analysis was carried out at weeks 1 and 2.

Each salt was maintained in a chamber kept at 40° C. with a relative humidity of 80%. The content of the active compound in each sample was examined by liquid chromatography after 1 and 2 weeks and compared with the initial values. The results are as follows:

| | Week 1 | Week 2 |
|---|---|---|
| sulfate (crystalline) | 98.4 | 96.8 |
| sulfate (non-crystalline) | 90.2 | 84.5 |
| hydrobromide | 95.4 | 87.4 |
| nitrate (crystalline) | 91.7 | 85.0 |
| p-toluenesulfonate | 27.9 | 4.4 |

The above results clearly show that the only one of the salts investigated by us which has sufficient stability for practical use is the crystalline sulfate.

We claim:

1. A storage-stable compound in crystalline form selected from the group consisting of 7-[2-(2-aminothiazol-4-yl)-(Z)-2-methoxyiminoacetamido]-3-[5-(2-hydroxyethyl)-4-methylthiazoliomethyl]-3-cephem-4-carboxylate sulfate, the crystals being characterised by the following X-ray diffraction data determined by the powder method using the copper $K_\alpha$-ray, $\lambda = 0.154$ nm with an error in measurement of relative intensity within ±5% (in this Table, d indicates crystal lattice and $I/I_{max}$ indicates relative intensity):

| Phase d | Relative intensity $I/I_{max}$ | Phase d | Relative intensity $I/I_{max}$ |
|---|---|---|---|
| 111.11 | 100 | 3.81 | 61 |
| 7.02 | 60 | 3.74 | 86 |
| 6.10 | 29 | 3.69 | 39 |
| 5.75 | 24 | 3.61 | 79 |
| 5.03 | 24 | 3.53 | 59 |
| 4.69 | 92 | 3.40 | 38 |
| 4.51 | 27 | 3.35 | 32 |
| 4.47 | 38 | 3.25 | 30 |
| 4.38 | 42 | 3.15 | 83 |
| 4.31 | 76 | 2.74 | 25 |
| 4.00 | 32 | 2.67 | 35 |
| 3.96 | 27 | | |

2. A method of preparing a compound as claimed in claim 1, which comprises adding dilute aqueous sulfuric acid, whilst cooling, to an aqueous solution of 7-[2-(2-aminothiazol-4-yl)-(Z)-2-methoxyiminoacetamido]-3-[5-(2-hydroxyethyl)-4-methylthiazoliomethyl]-3-cephem-4-carboxylate in an amount sufficient to provide at least an equimolar amount of sulfuric acid with respect to said 7-[2-(2-aminothiazol-4-yl)-(Z)-2-methoxyiminoacetamido]-3-[5-(2-hydroxyethyl)-4-methylthiazoliomethyl]-3-cephem-4-carboxylate and separating said compound as claimed in claim 1 from the reaction mixture.

3. The method of claim 2, in which the aqueous acid has a concentration of from 3% to 20% w/v.

4. The method of claim 2, in which the aqueous acid has a concentration of from 5% to 10% w/v.

5. The method of claim 2, in which the amount of acid is from 1 to 1.5 moles per mole of said 7-[2-(2-aminothiazol-4-yl)-(Z)-2-methoxyiminoacetamido]-3-[5-(2-hydroxyethyl)-4-methylthiazoliomethyl]-3-cephem-4-carboxylate.

6. The method of claim 2, in which the amount of acid is from 1.1 to 1.2 moles per mole of said 7-[2-(2-aminothiazol-4-yl)-(Z)-2-methoxyiminoacetamido]-3-[5-(2-hydroxyethyl)-4-methylthiazoliomethyl]-3-cephem-4-carboxylate.

7. A method of preparing a compound as claimed in claim 1, which comprises dissolving 7-[2-(2-aminothiazol-4-yl)-(Z)-2-methoxyiminoacetamido]-3-[5-(2-hydroxyethyl)-4-methylthiazoliomethyl]-3-cephem-4-carboxylate in water, and, whilst stirring the resulting solution on an ice bath, adding aqueous sulfuric acid having a concentration of from 3% to 20% w/v in an amount sufficient to provide from 1 to 1.5 mole of sulfuric acid, to the solution whilst cooling it with ice water, separating the resulting crystals by filtration, and washing them.

8. The method of claim 7, in which the separated crystals are washed with aqueous ethanol or ethanol and washed again with diethyl ether or water.

9. The method of claim 7, in which the crystals obtained are dried at 20° C. to 25° C.

10. The method of claim 7, in which the aqueous sulfuric acid has a concentration of from 5% to 10% w/v sulfuric acid and is employed in such an amount as to provide from 1.1 to 1.2 mole of sulfuric acid.

11. A method of preparing a compound as claimed in claim 1, which comprises dissolving an amorphous salt of 7-[2-(2-aminothiazol-4-yl)-(Z)-2-methoxyiminoacetamido]-3-cephem-4-carboxylate in water, neutralizing it with an alkali. and, whilst stirring the resulting solution on an ice bath, adding aqueous sulfuric acid having a concentration of from 3% to 20% w/v in an amount sufficient to provide from 1 to 1.5 mole of sulfuric acid, to the solution whilst cooling it with ice water, separating the resulting crystals by filtration, and washing them.

12. The method of claim 11, in which said amorphous salt is the amorphous sulfate, hydrochloride or nitrate.

13. The method of claim 11, in which said alkali is an alkali metal or alkaline earth metal carbonate or bicarbonate.

14. The method of claim 11, in which the separated crystals are washed with aqueous ethanol or ethanol and washed again with diethyl ether or water.

15. The method of claim 11, in which the crystals obtained are dried at 20° C. to 25° C.

16. The method of claim 11, in which the aqueous sulfuric acid has a concentration of from 5% to 10% w/v sulfuric acid and is employed in such an amount as to provide from 1.1 to 1.2 mole of sulfuric acid.

* * * * *

UNITED STATES PATENT AND TRADEMARK OFFICE
CERTIFICATE OF CORRECTION

PATENT NO. : 4,791,196
DATED : December 13, 1988
INVENTOR(S) : IDE et al

It is certified that error appears in the above-identified patent and that said Letters Patent is hereby corrected as shown below:

Column 3, line 51, "require" should read --required--.

Column 6, line 8, "phate. Phosphite" should read

-- phate, phospite --.

Column 8, line 8 (claim 11), after "2-methoxyiminoacetamido]-"

the following should be inserted:

-- 3-[5-(2-hydroxyethyl)-4-methylthiazoliomethyl] --

Signed and Sealed this

Thirty-first Day of July, 1990

Attest:

HARRY F. MANBECK, JR.

Attesting Officer

Commissioner of Patents and Trademarks